United States Patent
Bissery

(12) 
(10) Patent No.: US 6,441,026 B1
(45) Date of Patent: Aug. 27, 2002

(54) ANTITUMOR COMPOSITIONS CONTAINING TAXANE DERIVATIVES

(75) Inventor: Marie-Christine Bissery, Vitry sur Seine (FR)

(73) Assignee: Aventis Pharma S.A., Anthony Cedex (FR)

( * ) Notice: Subject to any disclaimer, the term of this patent is extended or adjusted under 35 U.S.C. 154(b) by 0 days.

(21) Appl. No.: 09/813,018

(22) Filed: Mar. 21, 2001

Related U.S. Application Data

(60) Continuation-in-part of application No. 09/705,739, filed on Nov. 6, 2000, which is a division of application No. 09/371,520, filed on Aug. 10, 1999, now Pat. No. 6,214,863, which is a continuation of application No. 09/182,900, filed on Oct. 30, 1998, now abandoned, which is a division of application No. 08/967,036, filed on Nov. 10, 1997, now Pat. No. 5,908,835, which is a division of application No. 08/424,470, filed on May 9, 1995, now Pat. No. 5,728,687.

(51) Int. Cl.⁷ ............................................. A61K 31/335
(52) U.S. Cl. ...................... 514/449; 514/184; 514/316; 514/410; 514/459
(58) Field of Search ................................ 514/184, 316, 514/410, 449, 459

(56) References Cited

U.S. PATENT DOCUMENTS

| | | | |
|---|---|---|---|
| 4,857,653 A | 8/1989 | Colin et al. | 549/511 |
| 4,876,399 A | 10/1989 | Holton et al. | 568/817 |
| 5,015,744 A | 5/1991 | Holton | 549/510 |
| 5,136,060 A | 8/1992 | Holton | 549/510 |
| 5,229,526 A | 7/1993 | Holton | 549/213 |
| 5,262,409 A | 11/1993 | Margolis et al. | 514/183 |
| 5,294,737 A | 3/1994 | Ojima | 562/444 |
| 5,466,834 A | 11/1995 | Holton | 549/510 |
| 5,494,683 A | 2/1996 | Liversidge et al. | 424/490 |
| 5,645,988 A | 7/1997 | Vande Woude et al. | 435/6 |
| 5,728,687 A | 3/1998 | Bissery | 514/90 |

FOREIGN PATENT DOCUMENTS

| | | |
|---|---|---|
| WO | WO 92/19765 | 11/1992 |

OTHER PUBLICATIONS

Rowinsky et al., Sequences of Taxol and Cisplatin: A Phase I and Pharmacologic Study, *J. of Clin. Oncology,* 9(9):1692–1703 (1991).

Rowinsky et al., The Clinical Pharmacology and Use of Antimicrotubule Agents in Cancer Chemotherapeutics, *Pharmac. Ther.,* 52:35–84 (1991).

Bissery et al., Abstract 2645, *Proceedings of the AACR,* 33:443 (Mar. 1992).

Bissery et al., "Preclinical Pro file of Docetaxel (Taxotere): Efficacy as a Single Agent and in Combination," *Seminars in Oncology,* 22(6)(Suppl 13):3–16 (1995).

Bissery et al., "The Taxoids," *Cancer Therapeutics: Experimetnal and Clinical Agents,* pp. 175–193 (1995).

Bissery et al., Abstract 1599, "Preclinical In Vivo Activ ity of Docetaxel Containing Combinations," *Proceedings of the ASCO,* 14:489 (1995).

Bissery et al., Abstract 50, "Preclinical In Vivo Ev aluation of Docetaxel (Taxotere®) Containing Combinations," *Proc. of the Cytoskeleton and Cancer,* p. 50 (Sep. 17–20, 1995).

Mirabelli et al., "A Murine Model to Evaluate the Ability of In Vitro Clonogenic Assays to Predict the Response to Tumors In Vivo," *Cancer Res.* 48:5447–5454 (1988).

Llombart–Cussac et al., Proceedings of ASCO, 16 (1997) Abstract No. 629.

*Primary Examiner*—Amelia Owens

(57) ABSTRACT

A pharmaceutical composition comprised of acetocyclopropyl taxotere or a derivatve thereof, and at least one of an alkylating agent, an antimetabolite, a spindle poison, an epidophyllotoxin, an antibiotic, an enzyme, a topoisomerase inhibitor, a platinum coordination complex, a biological response modifier or a growth factor inhibitor is described.

19 Claims, No Drawings

ANTITUMOR COMPOSITIONS CONTAINING TAXANE DERIVATIVES

This application is a continuation-in-part of U.S. patent application Ser. No. 09/705,739, filed Nov. 6, 2000, which is a divisional application of application Ser. No. 09/371,520, filed Aug. 10, 1999, now U.S. Pat. No. 6,214,863, which is a continuation application of application Ser. No. 09/182,900, filed Oct. 30, 1998, now abandoned, which is a divisional application of application Ser. No. 08/967,036, filed Nov. 10, 1997, now U.S. Pat. No. 5,908,835, which is a divisional application of application Ser. No. 08/424,470, filed May 9, 1995, now U.S. Pat. No. 5,728,687.

The present invention relates to combinations of taxol, Taxotere and their analogues and substances which are therapeutically useful in the treatment of neoplastic diseases.

Taxol, Taxotere and their analogues, which possess noteworthy antitumor and antileukemic properties, are especially useful in the treatment of cancers of the colon, ovary, breast or lung.

The preparation of taxol, Taxotere and their derivatives form the subject, for example, of European Patents EP 0,253,738 and EP 0,253,739 and International Application PCT WO 92/09,589.

Generally, the doses used, which depend on factors distinctive to the subject to be treated, are between 1 and 10 mg/kg administered intraperitoneally or between 1 and 3 mg/kg administered intravenously.

It has now been found, and this forms the subject of the present invention, that the efficacy of taxol, Taxotere and their analogues may be considerably improved when they are administered in combination with at least one substance which is therapeutically useful in anticancer treatments and has a mechanism identical to or different from this of taxane derivatives.

Among substances which may be used in association or in combination with taxol, Taxotere or their analogues, there may be mentioned alkylating agents such as cyclophosphamide, isosfamide, melphalan, hexametyl-melamine, thiotepa or dacarbazine, antimetabolites such as pyrimidine analogues, for instance 5-fluarouracil and cytarabine, or its analogues such as 2-flourodeoxycytidine, or folic acid analogues such as methotrexate, idatrexate or trimetrexate, spindle poisons including vinca alkaloids such as vinblastine or vincristine or their synthetic analogues such as navelbine, or estramustine or taxoids, epidophylloptoxins such as etoposide or teniposide, antibiotics such as daunorubicine, doxorubicin, bleomycin or mitomycin, enzymes such as L-asparaginase, topoisomerase inhibitors such as camptothecin derivatives chosen from CPT-11 and topotecan or pyridobenzoindole derivatives, and various agents such as procarbazine, mitoxantrone, platinum coordination complexes such as cisplatin or carboplatin, and biological response modifiers or growth factor inhibitors such as interferons or interleukins.

Moreover, since the activity of the products depends on the doses used, it is possible to use higher doses and to increase the activity while decreasing the toxicity phenomena or delaying their onset by combining growth factors of the haematopoietic type such as G-CSF or GM-CSF or certain interleukins with taxol, Taxotere, their analogues or their combinations with other therapeutically active substances.

The combinations or associations according to the invention enable the phenomena of pleiotropic resistance or "multi-drug resistance" to be avoided to delayed.

More especially, the invention relates to combinations of taxol, Taxotere and their analogues with vinca alkaloids, cyclophosphamide, 5-fluorouracil, doxorubicin, cisplatin, navelbine, camptothecin, and etoposide.

The improved efficacy of a combination according to the invention may be demonstrated by determination of the therapeutic synergy. A combination manifests therapeutic synergy if it is therapeutically superior to one or other of the constituents used at its optimum dose (T. H. Corbett et al., Cancer Treatment Reports, 66:1187 (1982)).

To demonstrate the efficacy of a combination, it may be necessary to compare the maximum tolerated dose of the combination with the maximum tolerated dose of each of the separate constituents in the study in question. This efficacy may be quantified, for example, by the $\log_{10}$ cells killed, which is determined according to the following formula:

$$\log_{10} \text{ cells killed} = T - C(\text{days})/3.32 \times T_d$$

in which T–C represents the time taken for the cells to grow, which is the mean time in days for the tumors of the treated group (T) and the tumors of the treated group (C) to have reached a predetermined value (1 g for example), and $T_d$ represents the time in days needed for the volume of the tumor to double in the control animals [T. H. Corbett et al., Cancer, 40, 2660–2680 (1977); F. M. Schabel et al., Cancer Drug Development, Part B, Methods in Cancer Research, 17, 3–51, New York, Academic Press Inc. (1979)]. A product is considered to be active if $\log_{10}$ cells killed is greater than or equal to 0.7. A product is considered to be very active if $\log_{10}$ cells killed is greater than 2.8.

The combination, used at its own maximum tolerated dose, in which each of the constituents will be present at a dose generally not exceeding its maximum tolerated dose, will manifest therapeutic synergy when the $\log_{10}$ cells killed is greater than the value of the $\log_{10}$ cells killed of the best constituent when it is administered alone.

The efficacy of the combinations on solid tumors may be determined experimentally in the following manner:

The animals subjected to the experiment, generally mice, are subcutaneously grafted bilaterally with 30 to 60 mg of a tumor fragment on day 0. The animals bearing tumors are mixed before being subjected to the various treatments and controls. In the case of treatment of advanced tumors, tumors are allowed to develop to the desired size, animals having insufficiently developed tumors being eliminated. The selected animals are distributed at random to undergo the treatments and controls. Animals not bearing tumors may also be subjected to the same treatments as the tumor-bearing animals in order to be able to dissociate the toxic effect from the specific effect on the tumor. Chemotherapy generally begins from 3 to 22 days after grafting, depending on the type of tumor, and the animals are observed every day. The different animal groups are weighed 3 or 4 times a week until the maximum weight loss is attained, and the groups are then weighed at least once a week until the end of the trial.

The tumors are measured 2 or 3 times a week until the tumor reaches approximately 2 g, or until the animal dies if this occurs before the tumor reaches 2 g. The animals are autopsied when sacrificed.

The antitumor activity is determined in accordance with the different parameters recorded.

For a study of the combinations on leukemias the animals are grafted with a particular number of cells, and the antitumour activity is determined by the increase in the survival time of the treated mice relative to the controls. The product is considered to be active if the increase in survival time is greater than 27%, and is considered to be very active if it is greater than 75% in the case of P388 leukemias.

The results obtained with combinations of Taxotere and various chemotherapeutic agents, such as cyclophosphamide (alkylating agent), 5-fluorouracil (antimetabolite), etoposide (semisynthetic podophyllotoxin agent) and vincristine (vinca alkaloid), the combinations being used at their optimum dose, are given as examples in the following tables.

TABLE 1

Activity of the combination Taxotere + cyclophosphamide at the optimum dose against advanced MA13/c mammary adenocarcinoma grafted subcutaneously

| Product | Dose mg/kg/injection i.v. | Administration on days: | Total dose mg/kg | $\log_{10}$ cells killed |
|---|---|---|---|---|
| Taxotere | 15 | 14, 17, 20 | 45 | 2.8 |
| Cylcophosphamide | 118 | 14 | 118 | 1.3 |
| Taxotere | 7.5 | 14, 17, 20, 14 | 22.5 | 3.4 |
| + cyclophosphamide | 90.0 | | 90 | |

TABLE 2

Activity of the combination Taxotere + etoposide at the optimum dose against advanced B16 melanoma grafted subcutaneously

| Product | Dose mg/kg/injection i.v. | Administration on days: | Total dose mg/kg | $\log_{10}$ cells killed |
|---|---|---|---|---|
| Taxotere | 17.5 | 4, 7, 10, 13 | 70 | 2.8 |
| Etoposide | 46.2 | 4, 7, 10, 13 | 184.8 | 1.3 |
| Taxotere | 15.7 | 4, 7, 10, 13 | 62.8 | 4.1 |
| + etoposide | 13.8 | (simultaneous) | 55.5 | |

TABLE 3

Activity of the combination Taxotere + 5-fluorouracil at the optimum dose against advanced C38 colon adenocarcinoma grafted subcutaneously

| Product | Dose mg/kg/injection i.v. | Administration on days: | Total dose mg/kg | $\log_{10}$ cells killed |
|---|---|---|---|---|
| Taxotere | 22 | 21, 25, 29, 33 | 88.0 | 1.4 |
| 5-fluorouracil | 43.4 | 21, 25, 29, 33 | 173.6 | 1.1 |
| Taxotere | 17.6 | 21, 25, 29, 33 | 70.4 | 4.8 |
| + 5-fluorouracil | 27.0 | (simultaneous) | 108.0 | |

TABLE 4

Activity of the combination Taxotere + vincristine at the optimum dose against advanced P388 leukemias ($10^6$ cells i.p.)

| Product | Dose mg/kg/injection i.v. | Administration on days: | Total dose mg/kg | $\log_{10}$ cells killed |
|---|---|---|---|---|
| Taxotere | 17.5 | 4, 7, 10, 13 | 70 | 2.8 |
| vincristine | 46.2 | 4, 7, 10, 13 | 184.8 | 2.8 |
| Taxotere | 21.75 | 1, 4, 7 | 65.25 | 62 |
| + vincristine | 1.2 | (simultaneous) | 3.6 | |
| Taxotere | 21.75 | 1, 4, 7 | 65.25 | 77 |
| + vincristine | 1.2 | (4 hours apart) | 3.6 | |

Experiments were also conducted using a taxotere analogue, N-debenzoyl-N-t-butoxy-carbonyl-7-deoxy-8-desmethyl-7, 8-cyclopropataxotere (hereinafter acetocyclopropyl taxotere) with several chemotherapeutic agents. The structure of acetocyclopropyl taxotere is as follows:

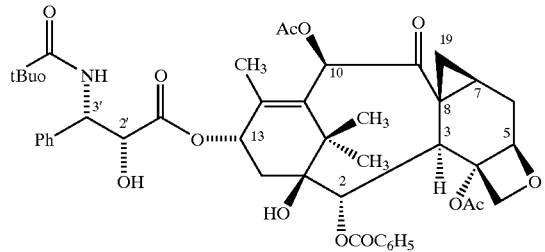

Combinations of acetocyclopropyl taxotere and various chemotherapeutic agents, such as doxorubicin (antibiotic), cisplatin (platinum coordination complex), navelbine (spindle poison), and CPT-11 (topoisomerase inhibitor), were evaluated in mice bearing s.c. transplantable tumors. The tumor model used to evaluate each drug combination was selected, in general, on the basis of its responsiveness to each of the agents when used as monotherapy. Using i.v. intermittent schedules, full dose response trials were conducted for each single agent and each combination.

In addition to the parameters described above, the combination toxicity index (CTI) was determined. See Corbett, T. H., et al., Response of transplantable tumors of mice to anthracenedione derivatives alone and in combination with clinically useful agents, Cancer Treat. Rep. 66: 1187–1200 (1982). The CTI represents the sum of the fractions of the lethal dose 10% ($LD_{10}$) of each single agent used in the optimal combination. It indicates the extent in host toxicity overlap. For example, a CTI of 1 indicates that only 50% of the $LD_{10}$ of each single agent (or any of the ratios, 70:30, 40:60, etc . . . ) can be used in combinations without incurring additional toxicity, whereas a CTI of 2 indicates that 100% of the $LD_{10}$ of each single agent can be used in combination.

The following table summarizes for each combination the therapeutic response and highest non toxic dose of each arm of the study, the single agents and the combination.

TABLE

Cyclopropatoxol combination trials at optimal dose.

| Agent (route of administration) | Tumor (implantation site) | Dose mg/kg/inj | Schedule (days) | Total dose mg/kg | % bwl loss at nadir (day of nadir) | T/C % | log cell kill | Responses | CTI |
|---|---|---|---|---|---|---|---|---|---|
|  |  |  |  |  |  |  |  | CR |  |
| acetocyclopropyl taxotere (IV) | Adv. MA13/C | 34.0 | 15,22 | 68.0 | 2.4 (19) | — | 2.9 | 3/5 |  |
| Doxorubicin (IV) | (SC) | 11.0 | 15,22 | 22.0 | 7.0 (26) | — | 3.0 | 3/5 |  |
| acetocyclopropyl taxotere A+ | Td = 2.6 days | 34.0 | simult. | 68.0 | 13.4 (27) | — | 5.3 | 5/5 | 1.42 |
| Doxorubicin |  | 11.0 |  | 22.0 |  |  |  |  |  |
|  |  | Median tumor size 81–116 mg |  |  |  |  |  |  |  |
|  |  |  |  |  |  |  |  | TFS |  |
| acetocyclopropyl taxotere (IV) | Early C51 | 30.0 | 5,12 | 60.0 | 10.7 (17) | 0 | 1.4 | 0/7 |  |
| Cisplatinum | (SC) | →3.1 |  | 6.2 | 4.8 (7) | 0 | 2.7 | 0/7 |  |
| acetocyclopropyl taxotere A + | Td = 2.5 days | 13.6 | simult. | 26.5 | 12.5 (16) | 0 | 3.6 | 2/7 | 0.68 |
| Cisplatinum |  | 2.0 |  | 4.0 |  |  |  |  |  |
| CPT-11 (PO) | Early C51 | 42.5 | 5,9 2x/d | 425.0 | 3.7 (7) | 0 | 1.1 | — |  |
| acetocyclopropyl taxotere A (IV) | (SC) | 21.1 | 5,9 | 42.2 | 8.6 (13) | 0 | 1.5 | — |  |
| CPT-11 (PO) + acetocyclopropyl taxotere (IV) | Td = 2 days | 21.0 11.9 | simult. | 210.0 23.8 | 8.3 (13) | 0 | 1.7 | — | 0.6 |
|  |  |  |  |  |  |  |  | TFS |  |
| acetocyclopropyl taxotere (IV) | Early MA 17/C | 40.3 | 5,12 | 80.6 | 3.5 (28) | 0 | 4.8 | 0/7 |  |
| Navelbine | (SC) | 16.0 | 5,12 | -320 | 11.8 (14) | 0 | 5.5 | 0/6 |  |
| acetocyclopropyl taxotere A + | Td = 1 day | 25.0 | 5,12 | 50.0 | 6.2 (17) | 0 | 8.1 | 2/7 | 1.42 |
| Navelbine |  | 16.0 | simult. | 32.0 |  |  |  |  |  |

Abbreviations used:
Td = tumor doubling time; bwl = body weight loss; TFS = tumor free survivors; CTI = combination toxicity; IV = intravenous; PO = by month; CR = Complete Response.

In combination with doxorubicin, the optimal combination produced a log cell kill of 5.3 in MA13/C bearing mice and induced 100% complete regressions (no cures) whereas the single agents produced lower log cell kill, i.e., acetocyclopropyl taxotere had a log cell kill of 2.9 and doxorubicin-3.0. The combination toxicity index was 1.42 indicating that approximately 70% of the HNTD of each single agent can be combined without additional toxicity.

With cisplatin, the optimal combination produced 3.6 log cell kill and 2/7 tumor free survivors on day 122 in Colon 51 bearing mice whereas the single agents produced 1.4 log cell kill for acetocyclopropyl taxotere and 2.7 log cell kill for cisplatin with no tumor free survivors. There was an important overlap in host recovery with a CTI of 0.68 indicating that less than 35% of each of the single agent can be administered in combination. However, the mice were not hyperhydrated when receiving cisplatin which may explain this degree of toxicity.

The combination of acetocyclopropyl taxotere with CPT-11 was found to be at least as good as the best single agent in the combinations (1.7 log cell kill for the combination, versus 1.5 for acetocyclopropyl taxotere and 1.1 for CPT-11). However, CTI of 0.6 indicates an important overlap in host toxicity.

Finally, there was a very good synergistic effect between acetocyclopropyl taxotere and navelbine in MA17/A bearing mice with a 8.1 log cell kill (and 2 tumor free survivors on day 123) for the combination, 4.8 for acetocyclopropyl taxotere and 5.5 for navelbine. The combination produced a modest overlap in host toxicity with a CTI of 1.42.

Overall, the four acetocyclopropyl taxotere combinations tested were all found synergistic i.e., the antitumor activity was greater in the combination arm than in single agent arm at highest non toxic dose.

In terms of tolerance, the combination of acetocyclopropyl taxotere with doxorubicin or navelbine, were well tolerated with a CTI of approximately 1.4, whereas dose reduction would be needed in the case of combination of cyclopropataxol with cisplatin or with CPT-11 (CTI<1).

The present invention also relates, therefore, to pharmaceutical compositions containing the combinations according to the invention.

The constituents of which the combination are composed may be administered simultaneously, semi-simultaneously, separately, or spaced out over a period of time so as to obtain the maximum efficacy of the combination; it being possible for each administration to vary in its duration from a rapid administration to a continuous perfusion.

As a result, for the purposes of the present invention, the combinations are not exclusively limited to those which are obtained by physical association of the constituents, but also to those which permit a separate administration, which can be simultaneous or spaced out over a period of time.

The compositions according to the invention are preferably compositions which can be administered parentally. However, these compositions may be administered orally or intraperitoneally in the case of localized regional therapies.

The compositions for parental administration are generally pharmaceutically acceptable, sterile solutions or suspensions which may optionally be prepared as required at the time of use. For the preparation of non-aqueous solutions or suspensions, natural vegetable oils such as olive oil, sesame oil or liquid petroleum or injectable organic esters such as ethyl oleate may be used. The sterile aqueous solutions can consist of a solution of the product in water. The aqueous solutions are suitable for intravenous administration provided the pH is appropriately adjusted and the solution is made isotonic, for example with a sufficient amount of sodium chloride or glucose. The sterilization may be carried out by heating or by any other means which does not adversely affect the composition. The combinations may also take the form of liposomes or the form of an association with carriers as cyclodextrins or polyethylene glycols.

The compositions for oral or intraperitoneal administration are preferably aqueous suspensions or solutions.

In the combinations according to the invention, the application of the constituents of which may be simultaneous, separate or spaced out over a period of time, it is especially advantageous for the amount of taxane derivative to represent from 10 to 90% by weight of the combination, it being possible for this content to vary in accordance with the nature of the associated substance, the efficacy sought and the nature of the cancer to he treated.

The combinations according to the invention are especially useful in the treatment of cancers of the colon, breast, ovary or lung, as well as melanoma and leukemia. In particular, they can afford the advantage of being able to employ the constituents at considerably lower doses than those at which they are used alone.

What is claimed is:

1. A pharmaceutical composition comprised of the compound of formula 1:

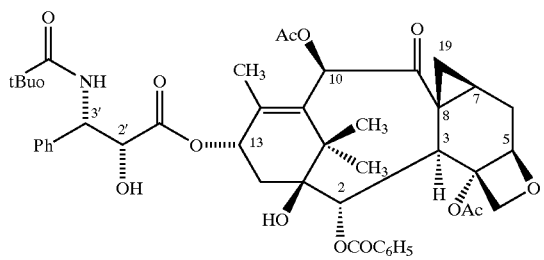

or a derivatve thereof, and at least one of an alkylating agent, an antimetabolite, a spindle poison, an epidophyllotoxin, an antibiotic, an enzyme, a topoisomerase inhibitor, a platinum coordination complex, a biological response modifier or a growth factor inhibitor.

2. The pharmaceutical composition according to claim 1 wherein the antibiotic agent is chosen from daunorubicin, doxorubicin, bleomycin and mitomycin.

3. The pharmaceutical composition according to claim 1 wherein the spindle poison is chosen from vinca alkaloids, their synthetic or semi-synthetic analogues, estramustine or navelbine.

4. The pharmaceutical composition according to claim 1 wherein the topoisomerase inhibitor is chosen from camptothecin and its derivatives including CPT-11, topotecan and pyridobenzoindole derivatives.

5. The pharmaceutical composition according to claim 1 wherein the platinum coordinating complex is chosen from cisplatin and carboplatin.

6. The pharmaceutical composition according to anyone of claims 2 to 5, further comprising growth factors of the haematopoietic type.

7. A method of administering the constituents of the composition as claimed in any one of claims 2 to 5, wherein said administration is separate and simultaneous.

8. A method of administering the constituents of the composition as claimed in any one of claims 2 to 5, wherein said administration is separate and sequential.

9. A method of administering the constituents of the composition as claimed in any one of claims 2 to 5, wherein said administration is separate and spaced out over time.

10. A pharmaceutical composition having therapeutic synergy in the treatment of neoplastic disease comprising a compound of the formula:

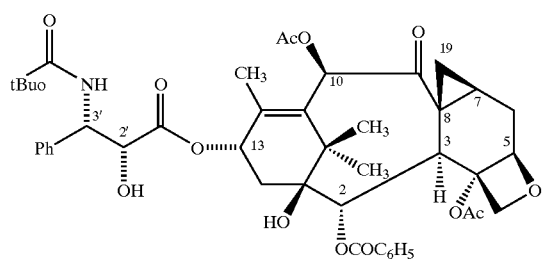

and doxorubicin.

11. A pharmaceutical composition having therapeutic synergy in the treatment of neoplastic disease comprising a compound of the formula:

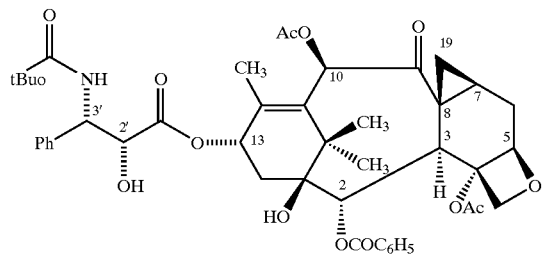

and navelbine.

12. A pharmaceutical composition having therapeutic synergy in the treatment of neoplastic disease comprising a compound of the formula:

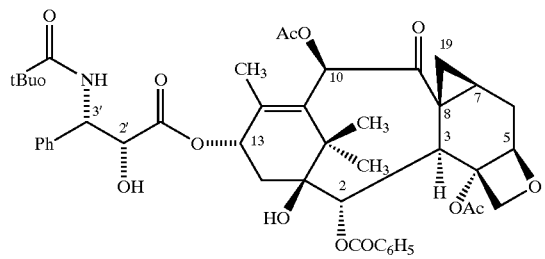

and cisplatin.

13. A pharmaceutical composition having therapeutic synergy in the treatment of neoplastic disease comprising a compound of the formula:

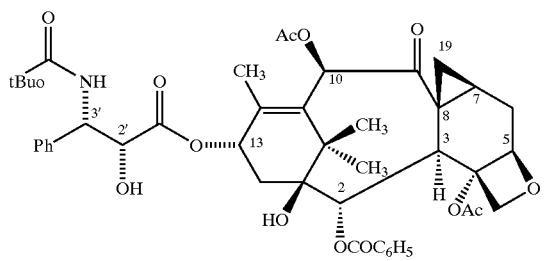

and CPT 11.

14. The pharmaceutical composition of any one of claims 10 to 13 wherein the constituents of the composition are administered simultaneously.

15. The pharmaceutical composition of any one of claims 10 to 13 wherein the constituents of the composition are administered separately and simultaneously.

16. The pharmaceutical composition of any one of claims 10 to 13 wherein the constituents of the composition are administered separately and semi-simultaneously.

17. The pharmaceutical composition of any one of claims 10 to 13 wherein the constituents of the composition are administered separately and sequentially.

18. The pharmaceutical composition of claim 10 or claim 11 wherein the neoplastic disease is breast cancer.

19. The pharmaceutical composition of claim 12 or claim 13 wherein the neoplastic disease is colon cancer.

* * * * *